(12) United States Patent
Kanner et al.

(10) Patent No.: US 9,492,643 B2
(45) Date of Patent: Nov. 15, 2016

(54) LOCKABLE SYRINGE AND METHOD OF ASSEMBLING SAME

(71) Applicant: Atrion Medical Products, Inc., Arab, AL (US)

(72) Inventors: Rowland W. Kanner, Guntersville, AL (US); Brian A. Roberts, Owens Cross Roads, AL (US)

(73) Assignee: Atrion Medical Products, Inc., Arab, AL (US)

( * ) Notice: Subject to any disclaimer, the term of this patent is extended or adjusted under 35 U.S.C. 154(b) by 247 days.

(21) Appl. No.: 14/204,980

(22) Filed: Mar. 11, 2014

(65) Prior Publication Data
US 2014/0343490 A1 Nov. 20, 2014

Related U.S. Application Data

(60) Provisional application No. 61/824,243, filed on May 16, 2013.

(51) Int. Cl.
*A61M 5/00* (2006.01)
*A61M 25/10* (2013.01)

(52) U.S. Cl.
CPC .... *A61M 25/10182* (2013.11); *A61M 25/1018* (2013.01); *Y10T 29/49881* (2015.01)

(58) Field of Classification Search
CPC ......... A61M 25/10182; A61M 25/20; A61M 25/108; A61M 25/1018
USPC .................................. 604/151, 97.02, 97.03
See application file for complete search history.

(56) References Cited

U.S. PATENT DOCUMENTS

| 4,832,692 A | * | 5/1989 | Box ................... A61M 25/1018 604/210 |
| 4,919,121 A | | 4/1990 | Rydell et al. |
| 5,047,015 A | | 9/1991 | Foote et al. |

(Continued)

FOREIGN PATENT DOCUMENTS

| WO | 92/07609 A1 | 5/1992 |
| WO | 97/44077 A1 | 11/1997 |

OTHER PUBLICATIONS

Extended European Search Report which issued in connection with corresponding European Application No. 14166784.0 on Aug. 28, 2014.

*Primary Examiner* — Edelmira Bosques
(74) *Attorney, Agent, or Firm* — Clark Hill PLC; James R. Foley

(57) ABSTRACT

A lockable syringe having an actuating mechanism for rapidly and selectively placing a movable thread bearing plunger member and stationary internally threaded cylinder into or out of threaded engagement, particularly for using the syringe to pressurize therapeutic medical balloon catheters, or the like. The mechanism includes a plunger having both a piston at its end to engage a barrel portion of a unitary syringe body, selectively deployable and retractable threaded segment, and an internally threaded cylindrical structure disposed within a unitary syringe body having a barrel. The plunger is engageable with the threaded cylinder by means of a threaded segment, and an operator actuated desmodromic arrangement to controllably reciprocate the threaded segment in a positive manner in order to allow either rapid manual or thread controlled plunger and piston movement within the syringe's barrel for purposes of displacing or pressurizing working fluid contained therein.

20 Claims, 7 Drawing Sheets

(56) References Cited

U.S. PATENT DOCUMENTS

| | | |
|---|---|---|
| 5,057,078 A | 10/1991 | Foote et al. |
| 5,209,732 A | 5/1993 | Lampropoulos et al. |
| 6,938,319 B2 | 9/2005 | Davis et al. |
| 2004/0122361 A1 | 6/2004 | Hart et al. |
| 2004/0247453 A1 | 12/2004 | Denolly |

* cited by examiner

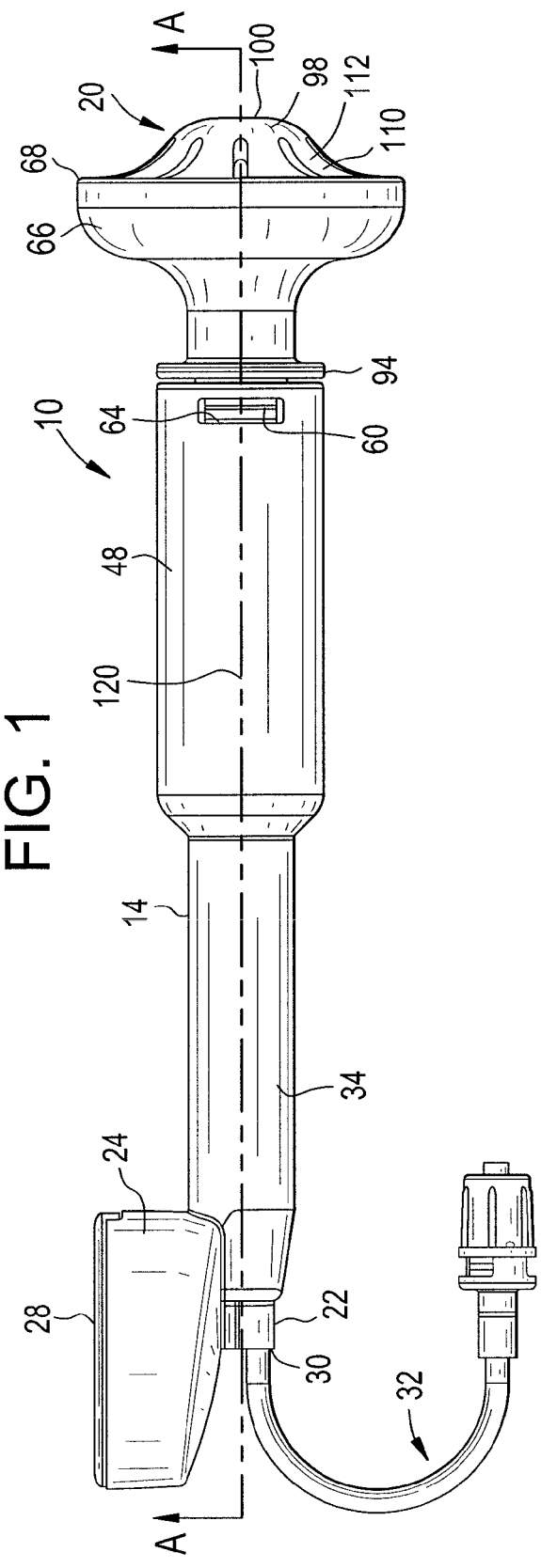

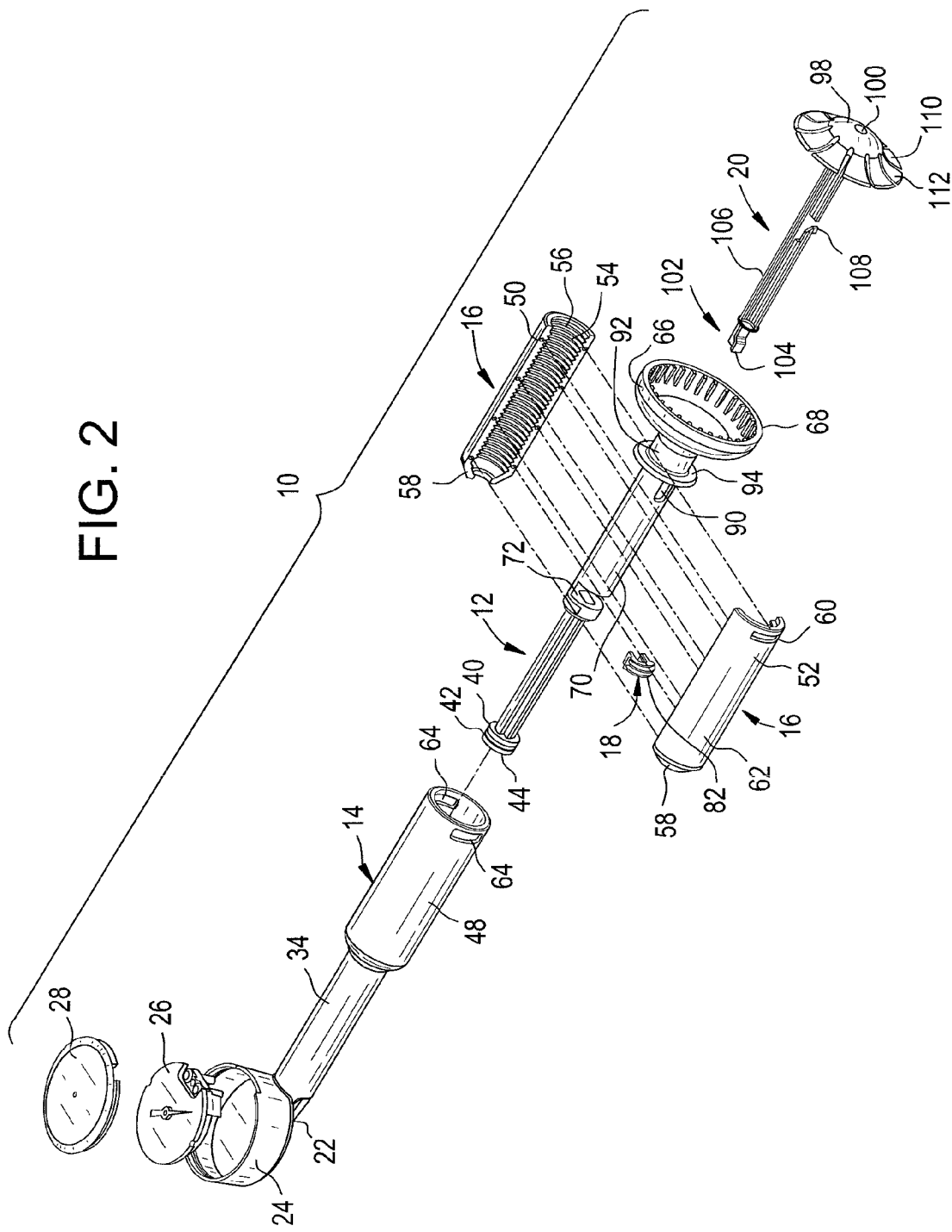

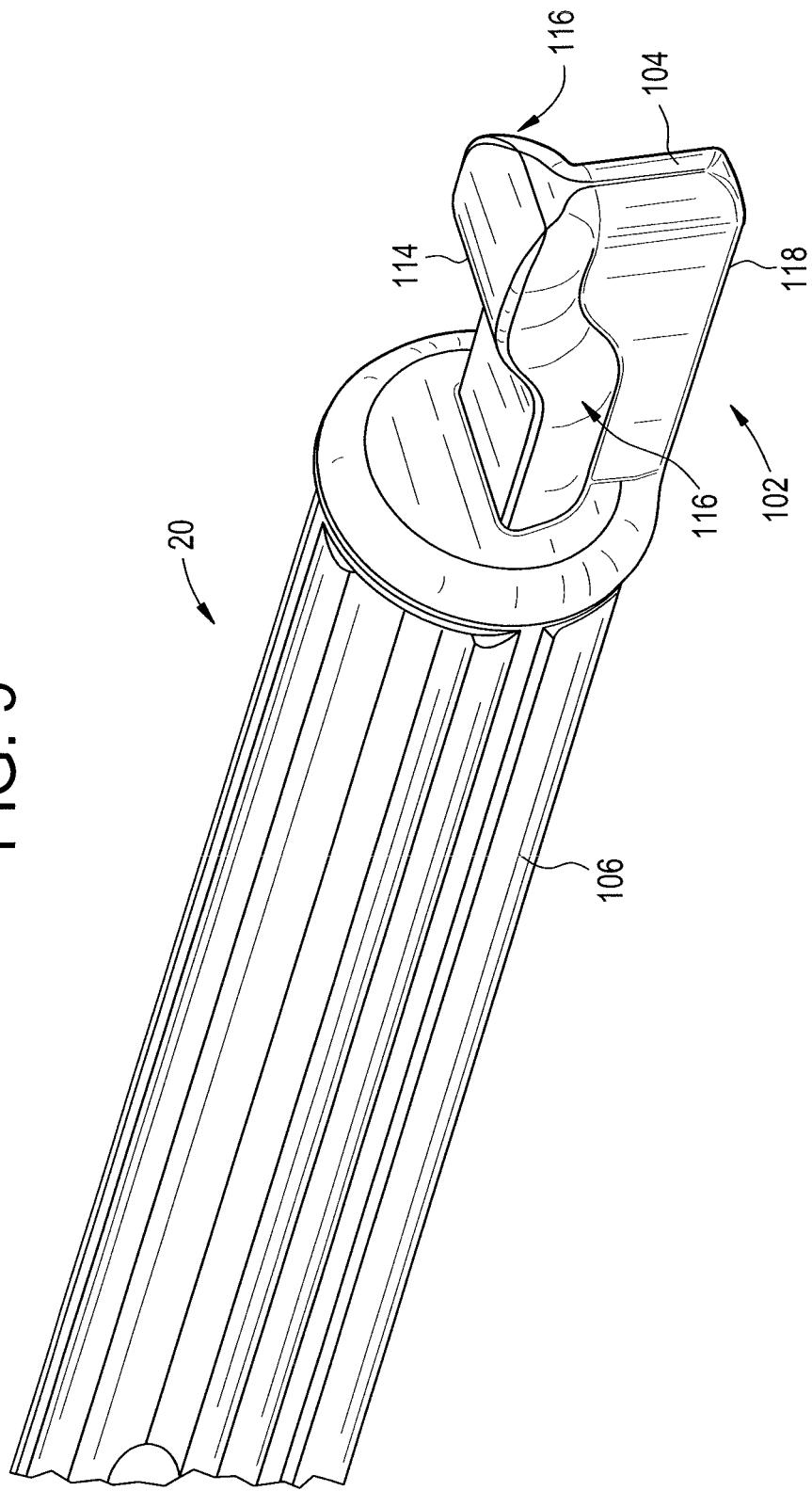

LOCKABLE SYRINGE AND METHOD OF ASSEMBLING SAME

RELATED APPLICATION (PRIORITY CLAIM)

This application claims the benefit of U.S. Provisional Application Ser. No. 61/824,243, filed May 16, 2013, which is hereby incorporated herein by reference in its entirety.

BACKGROUND

The present invention generally relates to lockable syringes for pressurizing medical devices, such as balloon catheters, as well as to methods of assembling lockable syringes.

During inflation of a balloon catheter, it is desirable for the medical provider to be able to easily and precisely control the pressure which is provided to the balloon. While it is desirable to be able to quickly apply or remove a substantial amount of pressure to or from the balloon, it is also desirable to be able to add just a little more pressure or remove just a little pressure from the balloon.

Lockable syringes (see, for example, the devices disclosed in U.S. Pat. Nos. 5,057,078 and 6,938,319) have become common in the medical field for precisely controlling the pressure which is applied to a balloon catheter. A typical lockable syringe provides that, in one state, a plunger is movable quickly into or out of a barrel, merely by pulling on a handle of the plunger. This causes a quick change in pressure with regard to the balloon catheter. On the other hand, the syringe can be placed in the locked position, thereby putting it in another state. In this other state, the handle of the plunger cannot be pushed or pulled. Instead, the handle must be rotated, thereby causing the plunger to slowly advance into or retract from the barrel. As such, the lockable syringe provides operation in effectively two states—a first state for macro movements, during which state the balloon catheter pressure can be changed greatly relatively quickly; and a second state for micro movements, during which state the balloon catheter pressure can be more precisely and slowly controlled.

While lockable syringes provide several advantages, many lockable syringes which are currently available for use in a balloon catheter procedure are difficult to use, difficult to assemble, and/or include too many parts.

SUMMARY

An object of an embodiment of the present invention is to provide a lockable syringe which is easy to use, easy to assemble, and does not include too many parts.

Briefly, an embodiment of the present invention provides a lockable syringe having an actuating mechanism for rapidly and selectively placing a movable thread bearing plunger member and stationary internally threaded cylinder into or out of threaded engagement, particularly for using the syringe to pressurize therapeutic medical balloon catheters, or the like. The mechanism includes a plunger having both a piston at its end to engage a barrel portion of a unitary syringe body, selectively deployable and retractable threaded segment, and an internally threaded cylindrical structure disposed within a unitary syringe body having a barrel. The plunger is engageable with the threaded cylinder by means of a threaded segment, and an operator actuated desmodromic arrangement to controllably reciprocate the threaded segment in a positive manner in order to allow either rapid manual or thread controlled plunger and piston movement within the syringe's barrel for purposes of displacing or pressurizing working fluid contained therein.

Except for radial insertion of the threaded segment into the plunger, all mechanism components of the lockable syringe are configured to provide for quick sequential axial assembly into the open rear of the unitary syringe body, preferably to be retained in place by snap together means of construction. The unitary syringe body, which is preferably entirely transparent to allow viewing of working fluid within its barrel and facilitate both filling and purging of entrained air in preparation for use, is preferably configured to provide an integral gauge housing for receiving a pressure gauge mechanism for operation in direct communication with the working fluid contained by the barrel. The barrel end of this housing is also preferably configured with a socket for receiving and bonding thereto a fluid delivery hose, said hose preferably being equipped with a Luer type connector for fluid tight coupling with medical balloon catheters and other therapeutic medical devices.

To use the lockable syringe, an operator pushes or pulls the control cam axially within the device in order to cause the threaded segment to either retract or deploy by means of its engagement with a deployment and retraction cam. Preferably, the control cam is restored to its rest position automatically by provision of a spring means biased in the return direction. For most applications, users of lockable syringes desire constant thread engagement as the default mode with disengagement as the option. In the preferred embodiment, the control cam resides within the center of the plunger, and therefore effectively within the center of the plunger's handle, placing its operator control surface in a convenient location for user access.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which:

FIG. 1 is a side view of a lockable syringe which is in accordance with an embodiment of the present invention, showing the lockable syrinfully assembled;

FIG. 2 is an exploded perspective view of the lockable syringe shown in FIG. 1;

FIG. 3 is a cross sectional view of the lockable syringe, taken along line A-A of FIG. 1, showing its plunger at full distal position, a control cam at rest and a threaded segment deployed in engagement with internal threads of a threaded cylinder;

FIG. 9 is a perspective view of a locking actuator of the lockable syringe, said end providing the control cam.

DESCRIPTION OF AN ILLUSTRATED EMBODIMENT

Figure 4:
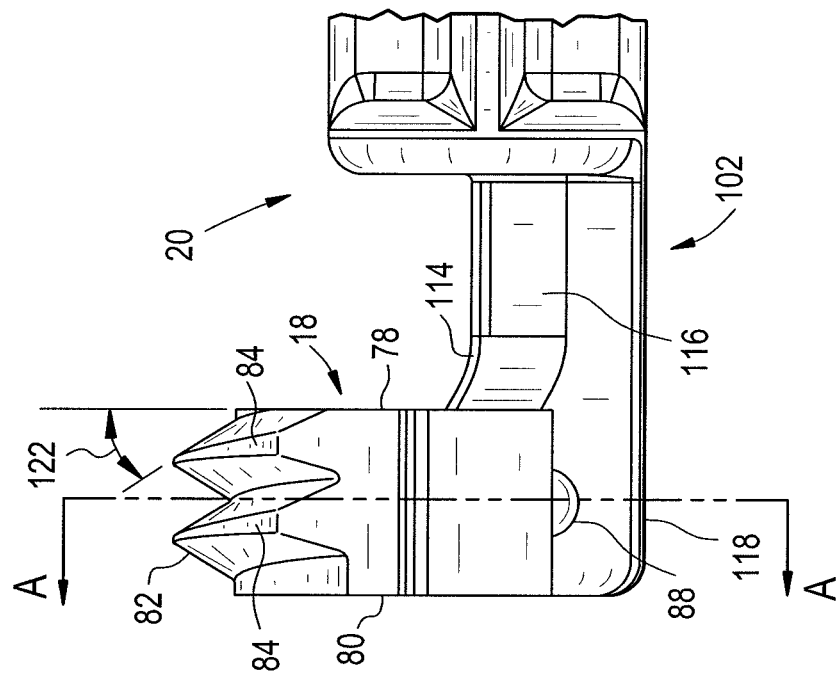
FIG. 4 is an enlarged view of a portion of the lockable syringe, showing the control cam assembled with the threaded segment in a deployed position and showing truncation of thread sections of the threaded segment to facilitate disengagement.

While this invention may be susceptible to embodiment in different forms, there is shown in the drawings and will be described herein in detail, a specific embodiment with the understanding that the present disclosure is to be considered an exemplification of the principles of the invention, and is not intended to limit the invention to that as illustrated.

FIG. 1 is a side view of a lockable syringe 10 which is in accordance with an embodiment of the present invention, while FIG. 2 provides an exploded view thereof. As shown, the lockable syringe 10 has very few parts. The basic components of the lockable syringe 10 include a plunger 12, a unitary syringe body 14, an internally threaded member such as a threaded cylinder 16, a threaded segment 18, and a locking actuator 20. Preferably, at an end 22 of the unitary syringe body 14 is an integral housing 24 for receiving a pressure gauge mechanism 26 as well as a protective lens 28 for protecting and sealing the pressure gauge mechanism 26 in the integral housing 24.

The unitary syringe body 14 also preferably includes a hose socket 30 proximate the integral housing 24 for receiving, for example, a hose and luer assembly 32 as shown in FIG. 1. The unitary syringe body 14 includes a syringe barrel 34 proximate the hose socket 30, as well as an internal port 36 (see FIG. 3) which effectively provides communication between the pressure gauge mechanism 26 and the working fluid within the syringe barrel 34.

Figure 6:
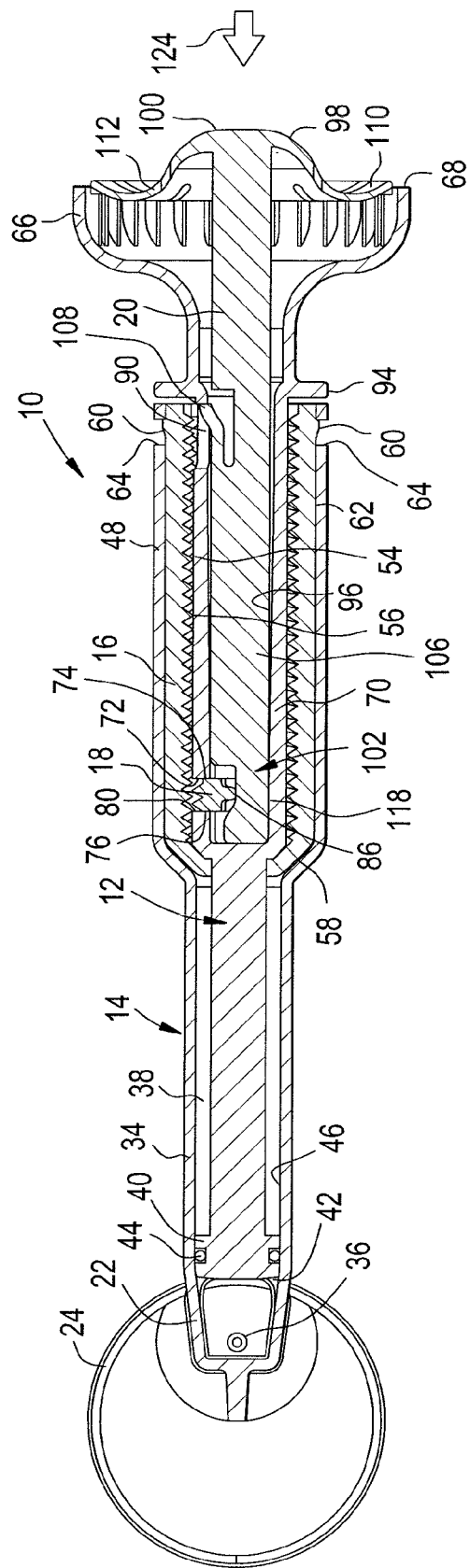
FIG. 6 is a cross sectional view similar to that of FIG. 3, but showing the plunger distal with the control cam operator control surface moved to deflect its return spring and position the engaged threaded segment in full retraction within the threaded cylinder.

The syringe barrel 34 is generally cylindrical and is configured to receive, in a passageway 38 provided therein, a piston 40 which is provided on the plunger 12, proximate one end 42 of the plunger 12. A seal 44 is provided on the piston 40, for sealing with an internal wall 46 of the syringe barrel 34 as shown in FIGS. 3 and 6. The unitary syringe body 14 also preferably includes a generally cylindrical portion 48 in which is disposed the threaded cylinder 16. As shown in FIG. 2, the threaded cylinder 16 is preferably provided in the form of two half segments 50, 52 which come together to from a generally cylindrical shape having a thread 54 on its internal surface 56. When the two half segments 50, 52 of the threaded cylinder 16 are mated, the threaded cylinder 16 effectively traps the piston end 42 of the plunger 12 via a close fitting distal end feature 58 of the threaded cylinder 16. Additionally, the unitary syringe body 14 effectively traps the segments 50, 52 of the threaded cylinder 16 therein, such that spreading apart of the segments 50, 52 due to outward radial force imparted by the threaded segment 18 during loading of the plunger 12 is prevented by the unitary syringe body 14 encompassing the segments 50, 52.

Additionally, retention means is provided between the generally cylindrical portion 48 of the unitary syringe body 14 and the threaded cylinder 16, for generally retaining the threaded cylinder 16 to the unitary syringe body 14 and preventing the threaded cylinder from rotating within the unitary syringe body 14. As shown in FIGS. 1-3 and 6, the retention means may be provided in the form of tabs 60 on the external surface 62 of the threaded cylinder 16 (i.e., a tab 60 on each half segment 50, 52) which are received in corresponding notches 64 in the generally cylindrical portion 48 of the unitary syringe body 14. Additional or alternative retaining means may be provided between the threaded cylinder 16 and the unitary syringe body 14. For example, flanges may be provided along the abutting faces of the threaded cylinder 16 for receipt in corresponding grooves in the unitary syringe body 14. Such a configuration would not only tend to prevent the threaded cylinder 16 from rotating relative to the unitary syringe body 14, but would tend to push the two half segments 50, 52 of the threaded cylinder 16 together.

While the plunger 12 has a piston 40 proximate the one end 42 of the plunger 12, preferably a handle 66 is provided proximate the opposite end 68. The handle 66 is shaped and configured to be controlled by an operator using his or her hand. The plunger 12 includes a generally cylindrical portion 70, and a receptacle 72 is provided in the generally cylindrical portion 70. The threaded segment 18 is received in the receptacle 72. Sidewalls 74, 76 of the receptacle 72 function to retain and guide the threaded segment 18. The threaded segment 18 includes thrust faces 78, 80 (see FIGS. 4, 7 and 8) which bear against the sidewalls 74, 76 of the receptacle 72 (see FIGS. 3 and 6). The threaded segment 18 is configured to traverse radially within the receptacle 72 and includes thread elements 82. The thread elements 82 are preferably truncated (as indicated by reference numeral 84 in FIGS. 4 and 8) and configured to selectively engage and disengage the thread 54 which is provided on the internal surface 56 of the threaded cylinder 16, thereby locking and unlocking the lockable syringe 10. This will be described in more detail later hereinbelow. In addition to the thread elements 82 and thrust faces 78, 80, the threaded segment 18 also includes a deployment cam follower 86 (see FIGS. 5, 7 and 8) and a retraction cam follower 88 (see FIGS. 4, 5, 7 and 8).

Preferably, the generally cylindrical portion 70 of the plunger 12 also includes a notch 90, and an external surface 92 of the plunger 12 provides an outwardly extending flange 94. The generally cylindrical portion 70 of the plunger 12 has an internal passageway 96 which receives the locking actuator 20.

The locking actuator 20 preferably includes an operator interface surface 98 at one end 100, and a control cam 102 at the other end 104 (see FIG. 9). The locking actuator 20 includes a shaft-like portion 106 which includes a retention feature 108. This retention feature 108 may take the form of a finger which effectively mates with the notch 90 in the plunger 12, thereby providing that the locking actuator 20 is generally locked with the plunger 12, but is generally slidable for a pre-determined distance relative thereto (i.e., depending on the length of the notch 90, etc.), wherein the finger 108 on the locking actuator 20 moves along the notch 90 in the plunger 12. The locking actuator 20 also preferably includes spring means 110 for biasing the locking actuator 20 to the retracted position relative to the plunger 12. This spring means 110 may be provided proximate or on the operator interface surface 98, in the form of an arcuate, multi-segmented, flexible wall 112, which tends to push the locking actuator 20 to the retracted position relative to the plunger 12.

The control cam 102 of the locking actuator 20 comprises a deployment cam 114 (see FIGS. 4-6 and 9) and a retraction cam 116 (see FIGS. 4, 5, 7 and 9), both of which are configured to engage the cam followers 86, 88 of the threaded segment 18. Additionally, the control cam 102 includes a heel 118 (see FIGS. 4-7 and 9). The deployment cam 114 is configured to effectively push the threaded segment 18 into threaded engagement with the thread 54 on the threaded cylinder 16, as shown in FIG. 3, thereby effectively threadably locking the plunger 12 relative to the threaded cylinder 16. In this state, the handle 66 of the plunger 12 cannot be pushed or pulled relative to the unitary syringe body 14 and instead must be rotated to effect micro-movement of the plunger 12 resulting in small, controlled changes in pressure. In contrast, the retraction cam 116 is configured to allow the threaded segment 18 to threadably disengage from the thread 54 on the threaded cylinder 16, as shown in FIG. 6, thereby effectively unlocking the plunger 12 relative to the threaded cylinder 16. In this state, the handle 66 of the plunger 12 can be pushed or pulled relative to the unitary syringe body 14 to effect macro-movement of the plunger 12 resulting in large pressure changes.

In order to achieve rapid fluid delivery and pressure build without the undesirable penalties of a large high pitch control thread, the lockable syringe 10 disclosed herein is preferably provided with a multiple lead control thread (i.e., with regard to thread elements 82 and thread 54). Therefore, thread pitch or the amount of plunger travel per complete rotation, can range for instance from 0.100" to a preferred 0.166" for double lead threads and even 0.250" for a triple lead thread without any penalty for the excessive thread depth typically common to such steeply pitched threads. An additional benefit to this approach is that multiple lead threads allow operators transitioning from manual plunger movement to controlled thread engagement to do so in a manner that is transparent and normal feeling, for example, a 0.166" dual lead thread offers a thread engagement point at every 0.083" of plunger travel just as is the case with a single lead control thread of 0.083" pitch. By comparison, this would certainly not be true if using a single lead thread of 0.166" pitch which only engages once for every 0.166" of plunger travel. A further benefit of the multiple lead control thread is that its shallower depth also requires less transverse retraction movement of the plunger's threaded segment 18 for complete disengagement. Still yet another benefit of the shallower multiple lead threads when compared to deeper single lead threads of similar pitch is the economy they present in terms of overall device girth in order to allow small displacement devices to be designed compactly.

Although the threaded segment 18 is described and shown in the drawings as having two thread elements 82, the threaded segment 18 can be provided as having only a single thread element or even several, as dictated by the load it is expected to withstand in use and the rate of advancement desired per plunger revolution. Regardless, the threaded segment 18 is retained and guided by parallel sidewalls 74, 76 of the receptacle 72, as shown in FIG. 3. Load resulting from pressure of working fluid resisting piston advancement within the barrel 34 is in line with the longitudinal axis (indicated with horizontal line 120 in FIG. 1) of the device 10 and transfers from the face of the receptacle's sidewall 76 nearest the barrel 34 to the adjacent thrust face 80 of threaded segment 18, and then sequentially to thread elements 82 engaged with the thread 54 of the threaded cylinder 16, and finally to the unitary syringe body 14, housing and retaining same through engagement of the retention features 60 on the threaded cylinder 16 with the corresponding notches 64 in the unitary syringe body 14. Loading under vacuum conditions within the barrel 34 results in the opposite sidewall 74 of the receptacle 72 bearing against the thrust face 78 of the threaded segment 18 and the same chain of load transfers occurring in the opposite direction. In order to assure complete and simultaneous engagement and disengagement of the threaded segment 18 from the threaded cylinder 16, its thread elements 82 are preferably truncated (as indicated by reference numeral 84 in FIG. 4) by a radius preferably equal to but not exceeding that of an imaginary cylinder inscribed within and touching the crests of the thread 54 of the threaded cylinder 16. This truncation assures that the tips of the threaded segment's thread elements 82 release from the threaded cylinder 16 simultaneously with their center which prevents fretting of the thread elements' ends during release and reduces the amount of transverse travel distance and therefore cam height required for threaded segment 18 engagement and disengagement. Further, angle 122 (see FIG. 4) describing the slope of the thread's form in cross section serves to assist the cam in retraction of the threaded segment 18 during release from load by imparting a longitudinal thrust against the threaded segment 18 urging it to retract inward. The degree of this assistance can be controlled by means of angle 122, chosen during thread design.

Figure 7:
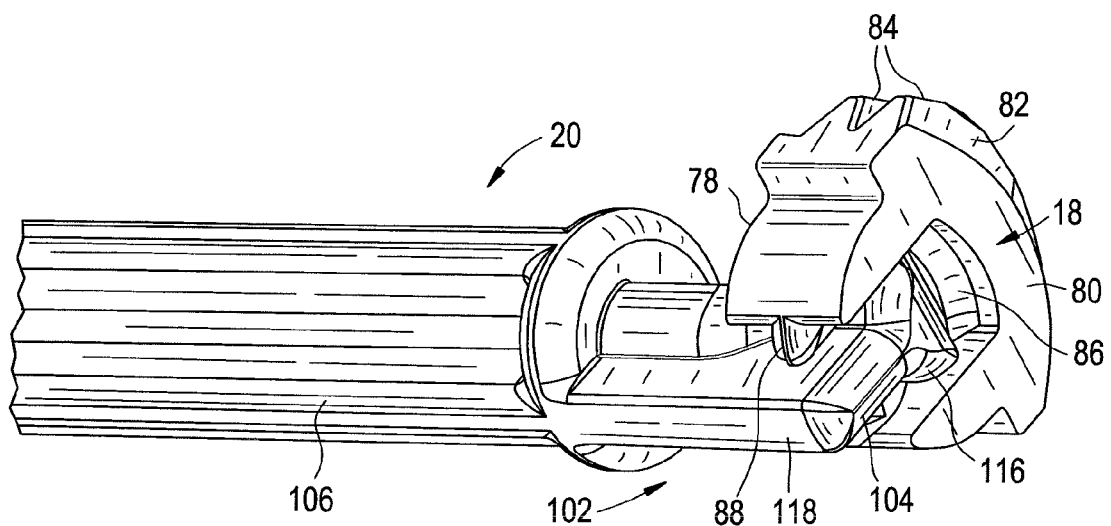
FIG. 7 is a perspective view of a portion of the lockable syringe, showing the control cam engaged with the threaded segment in a deployed position and showing both engagement and retraction cam followers and thrust faces of the threaded segment.
Figure 8:
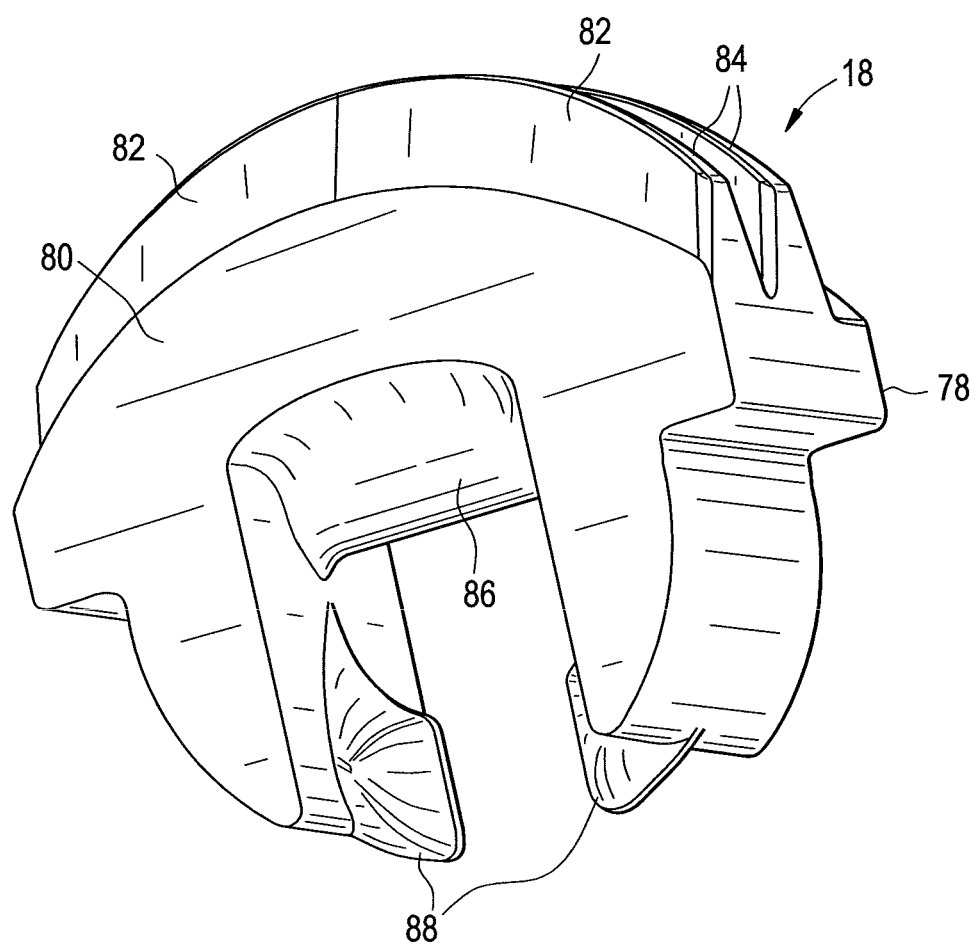
FIG. 8 is a perspective view of the threaded segment of the lockable syringe.

When loaded from generation of fluid pressure in use, the threaded segment's deployment cam follower 86, as shown in FIG. 7, presses against deployment cam 114 and this thrust which is transverse to the syringe axis 120 is resisted by heel 118 of the cam's supporting structure which bears against the inner wall of the plunger structure containing it and in turn transfers its load to the surrounding thread 54 of the threaded cylinder 16, which then transfers this transverse load to the unitary syringe body 14, surrounding and containing it. Retraction of threaded segment 18 does not depend upon reactive thrust under load; however, the interaction of deployment cam 114, retraction cam 116 and threaded segment 18 is desmodromic in nature and therefore capable of positively reciprocating threaded segment 18 inward or outward, as shown in FIG. 6, such that when the control cam's operator interface surface 98 is actuated (as indicated by arrow 124 in FIG. 6), threaded segment 18 is pulled inward thereby disengaging it. This movement is accomplished through engagement of retraction cam follower 88 of threaded segment 18 with retraction cam 116 positioned behind deployment cam 114. It should be noted that during operator movement of control cam 102, its retention feature 108 remains free to traverse longitudinally within the notch 90 in the plunger 12.

Motion of the threaded segment 18 during deployment or retraction by cam 102 could be at any angle up to that of the angle of the individual thread form, but for purposes of resolving resulting vector forces under load, sidewalls 74, 76 of the receptacle 72 are preferably positioned to keep motion of the threaded segment 18 transverse to longitudinal axis 120 of the plunger 12. The aspect ratio of the height of the threaded segment 18 across its thrust faces 78, 80 to its depth of engagement within the receptacle 72 is preferably kept to 1.0 or less in order to assure that threaded segment 18 remains as perpendicular to the plunger's longitudinal axis 120 as possible while maintaining reasonable operating clearances between these parts. Additional height across these thrust faces 78, 80 without an increase in their depth of engagement would result in higher angular deflection forces potentially leading to increased misalignment of the threaded segment 18 and jamming This would place more load on retraction cam 116 when called upon to withdraw the threaded segment 18 while operating under full pressure load. Another concern resulting from an undesirable aspect ratio is that full retraction would become more difficult due to allowable angular motion that results from necessary operating clearances between receptacle and segment components. This angular motion could cause tips of the thread 54 of the threaded segment 18 to not disengage squarely or completely and therefore impair free movement by dragging within the threaded cylinder 16.

Figure 5:
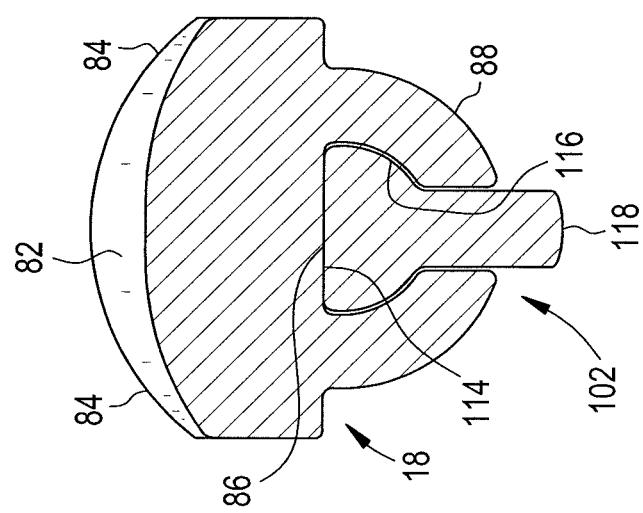
FIG. 5 is a cross sectional view, taken along line A-A of FIG. 4, of the threaded segment assembled on the control cam in the deployed position and showing relationship of the cam's surfaces to the cam followers of the threaded segment.

Another aspect of the present invention provides a method of assembling the device. Beginning with plunger 12, assembly is accomplished by installing seal 44 on piston 40, inserting threaded segment 18 into receptacle 72 of plunger 12, inserting control cam 102 axially into plunger 12 to engage the cam followers 86, 88 of the threaded segment 18 (as shown in FIGS. 4, 5 and 7) with deployment and retraction cams 114, 116, bringing control cam return spring means 110 into contact with plunger 12 and allowing the threaded cylinder's retention features 60 to lock into the notches 64 on the plunger 12. If desired, a decorative cover ring (not shown) may be pressed onto handle 66 of the plunger 12, i.e., for aesthetic purposes. It should also be noted that although control cam 102 is illustrated herein with spring means 110 formed integrally with control cam's operator control surface 98, those skilled in the art will recognize that use of a common wound wire spring interposed between plunger 12 and operator control surface 98 would accomplish the same purpose as the integral spring means 110 on operator control surface 98, although doing so would be at the expense of one additional component. Still other structures are entirely possible to achieve this function. The entire plunger sub assembly is next enveloped by the threaded cylinder 16, thereby completing the operator control and drive sub-assembly. Once plunger 12 is enveloped by the threaded cylinder 16, the piston 40 end of the plunger 12 becomes trapped by close fitting distal end feature 58 of the threaded cylinder 16, thereby preventing piston 40 from being able to be removed from the threaded cylinder 16. This completed control and drive assembly is then inserted into unitary syringe body 14, first by engaging piston 40 and seal 44 with barrel 34 before pressing the control and drive assembly home axially whereby threaded cylinder 16 is then snugly captured within syringe body 14 and secured in place by engagement of its snap type retaining features 60 with the corresponding notches 64 provided in the unitary syringe body 14. Following installation of the syringe actuating components, the pressure gauge mechanism 26 is secured within its integral housing 24 proximate the end 22 of the unitary syringe body 14, the protective lens 28 is snapped into place over it, and a Luer equipped hose assembly 32 is bonded into the receiving socket 30. If desired, either or both the pressure gauge mechanism 26 and the Luer equipped hose assembly 32 may be assembled to the unitary syringe body 14 first before proceeding with installation of the operator control and drive sub assembly.

While a specific embodiment of the present invention has been shown and described, it is envisioned that those skilled in the art may devise various modifications without departing from the spirit and scope of the present invention.

What is claimed is:

1. A lockable syringe for pressurizing a medical device, said lockable syringe comprising: an internally threaded member; a plunger, wherein at least a portion of the plunger is in the internally threaded member; a member having an external thread thereon, said member being carried by the plunger; a locking actuator which extends into the plunger and engages the member having the external thread thereon, wherein the locking actuator is actuatable to disengage the member having the external thread thereon from the internally threaded member, thereby allowing the plunger to slide relative to the internally threaded member, without having to rotate the plunger, wherein the member having the external thread thereon is carried in a receptacle in the plunger, wherein the member is moveable within the receptacle, into and out of engagement with the internally threaded member, further comprising a unitary syringe body, wherein the internally threaded member comprises a plurality of segments which are disposed in the unitary syringe body, wherein spreading apart of the segments of the internally threaded member due to outward radial force imparted by the threaded segment during loading of the plunger is prevented by the unitary syringe body encompassing the segments of the internally threaded member.

2. A lockable syringe as recited in claim 1, wherein the locking actuator is pushable to disengage the member having the external thread thereon from the internally threaded member, and wherein the locking actuator is biased out of the plunger.

3. A lockable syringe as recited in claim 1, wherein the plunger comprises a notch, and the locking actuator comprises a finger which moves along the notch.

4. A lockable syringe as recited in claim 1, wherein the unitary syringe body comprises a passageway, wherein the plunger comprises a piston, wherein said piston is moveable within the passageway of the unitary syringe body.

5. A lockable syringe as recited in claim 1, wherein the lockable syringe is configured such that the internally threaded member is prevented from substantially rotating relative to the unitary syringe body.

6. A lockable syringe as recited in claim 1, wherein the piston comprises a handle at one end thereof and a piston at an opposite end thereof.

7. A lockable syringe as recited in claim 1, wherein the locking actuator comprises an operator interface surface at one end thereof, and a control cam at an opposite end thereof.

8. A lockable syringe as recited in claim 7, wherein the operator interface surface of the locking actuator comprises spring means configured to bias the locking actuator out of the plunger such that the member having the external thread thereon engages the internally threaded member.

9. A lockable syringe as recited in claim 7, wherein the control cam comprises a deployment cam and a retraction cam.

10. A lockable syringe as recited in claim 9, wherein the deployment cam is configured to push the member having the external thread thereon into threaded engagement with the internally threaded member thereby locking the plunger, and the retraction cam is configured to allow the member having the external thread thereon to threadably disengage from the internally threaded member thereby unlocking the plunger.

11. A lockable syringe as recited in claim 10, wherein the member having the external thread comprises a deployment cam follower and a retraction cam follower.

12. A lockable syringe as recited in claim 1, wherein the plunger has a longitudinal axis, wherein the receptacle is defined by sidewalls which tend to keep motion of the threaded member transverse to a longitudinal axis of the plunger.

13. A lockable syringe as recited in claim 1, said unitary syringe body comprising an integral gauge housing for receiving a pressure gauge mechanism and an internal fluid communicating port to deliver working fluid within the syringe to the pressure gauge mechanism.

14. A method of assembling a lockable syringe, said method comprising: providing a syringe body; providing an internally threaded member; providing a plunger; providing a member having an external thread thereon; providing a locking actuator; engaging the member having the external thread thereon with the plunger; inserting the locking actuator into the plunger such that the locking actuator engages the member having the external thread; assembling the internally threaded member such that the internally threaded member becomes formed around the plunger, thereby forming a subassembly; and inserting the subassembly into the syringe body such that a radially external surface of the internally threaded member engages the syringe body such that the internally threaded member is prevented from substantially rotating relative to the syringe body, wherein the method provides that the member having the external thread thereon is carried in a receptacle in the plunger, wherein the member is moveable within the receptacle, into and out of engagement with the internally threaded member.

15. A lockable syringe for pressurizing a medical device, said lockable syringe comprising: an internally threaded member; a plunger, wherein at least a portion of the plunger is in the internally threaded member; a member having an external thread thereon, said member being carried by the plunger; a locking actuator which extends into the plunger and engages the member having the external thread thereon, wherein the locking actuator is actuatable to disengage the member having the external thread thereon from the internally threaded member, thereby allowing the plunger to slide relative to the internally threaded member, without having to rotate the plunger, further comprising a unitary syringe body, wherein the internally threaded member comprises a plurality of segments which are disposed in the unitary syringe body, wherein spreading apart of the segments of the internally threaded member due to outward radial force imparted by the threaded segment during loading of the plunger is prevented by the unitary syringe body encompassing the segments of the internally threaded member.

16. A lockable syringe as recited in claim 15, wherein the locking actuator is pushable to disengage the member having the external thread thereon from the internally threaded member, and wherein the locking actuator is biased out of the plunger.

17. A lockable syringe as recited in claim 15, wherein the plunger comprises a notch, wherein the locking actuator comprises a finger which moves along the notch, wherein the unitary syringe body comprises a passageway, wherein the plunger comprises a piston, wherein said piston is moveable within the passageway of the unitary syringe body.

18. A lockable syringe as recited in claim 15, wherein the locking actuator comprises an operator interface surface at one end thereof, and a control cam at an opposite end thereof, wherein the operator interface surface of the locking actuator comprises spring means configured to bias the locking actuator out of the plunger such that the member having the external thread thereon engages the internally threaded member.

19. A lockable syringe as recited in claim 18, wherein the control cam comprises a deployment cam and a retraction cam, wherein the deployment cam is configured to push the member having the external thread thereon into threaded engagement with the internally threaded member thereby locking the plunger, and the retraction cam is configured to allow the member having the external thread thereon to threadably disengage from the internally threaded member thereby unlocking the plunger, wherein the member having the external thread comprises a deployment cam follower and a retraction cam follower.

20. A lockable syringe as recited in claim 15, wherein the unitary syringe body comprises an integral gauge housing for receiving a pressure gauge mechanism and an internal fluid communicating port to deliver working fluid within the syringe to the pressure gauge mechanism.

\* \* \* \* \*